(12) United States Patent
Andersen

(10) Patent No.: US 9,629,654 B2
(45) Date of Patent: Apr. 25, 2017

(54) THROMBUS REMOVAL APPARATUS

(71) Applicant: COOK MEDICAL TECHNOLOGIES LLC, Bloomington, IN (US)

(72) Inventor: Torben Peter Andersen, Taastrup (DK)

(73) Assignee: Cook Medical Technologies LLC, Bloomington, IN (US)

( * ) Notice: Subject to any disclaimer, the term of this patent is extended or adjusted under 35 U.S.C. 154(b) by 349 days.

(21) Appl. No.: 13/786,984

(22) Filed: Mar. 6, 2013

(65) Prior Publication Data
US 2014/0214059 A1    Jul. 31, 2014

(30) Foreign Application Priority Data

Jan. 28, 2013    (GB) .................................. 1301428.7

(51) Int. Cl.
| | | |
|---|---|---|
| *A61B 17/3207* | (2006.01) | |
| *A61B 17/22* | (2006.01) | |
| *A61B 17/00* | (2006.01) | |
| *A61B 17/32* | (2006.01) | |

(52) U.S. Cl.
CPC ............ *A61B 17/320758* (2013.01); *A61B 17/22012* (2013.01); *A61B 17/3207* (2013.01); *A61B 2017/00398* (2013.01); *A61B 2017/00415* (2013.01); *A61B 2017/22021* (2013.01); *A61B 2017/320028* (2013.01)

(58) Field of Classification Search
CPC ........ A61B 17/3207; A61B 17/320016; A61B 10/04; A61B 2010/045; A61B 5/15123; A61F 9/00745; A61F 9/00763

USPC ....... 606/127–129, 159, 164, 167, 169, 170, 606/99, 200; 604/22

See application file for complete search history.

(56) References Cited

U.S. PATENT DOCUMENTS

| | | | | |
|---|---|---|---|---|
| 5,476,100 A | * | 12/1995 | Galel | .............................. 600/466 |
| 5,520,635 A | | 5/1996 | Gelbfish | |
| 5,906,623 A | * | 5/1999 | Peterson | ....................... 606/128 |

(Continued)

FOREIGN PATENT DOCUMENTS

WO    WO 02/100460 A2    12/2002

OTHER PUBLICATIONS

Combined Search and Examination Report under Sections 17 and 18(3) for related GB patent application No. GB1301428.7 mailing date May 22, 2013.

*Primary Examiner* — Katherine Rodjom
(74) *Attorney, Agent, or Firm* — Brinks Gilson & Lione

(57) ABSTRACT

A thrombus removal apparatus (10) includes a catheter (12) having at its distal end (14) a solenoid coil section (16) within which there is disposed a piercing element (20) made of electromagnetic material. Within the solenoid coil section (16) there is provided a solenoid coil (26) which can be powered to generate an electromagnetic field which causes the piercing element (20) to reciprocate into and out of the coil section (16), in practice to pierce into and fragment a thrombus disposed in a patient's vessel. An aspiration unit may be provided for aspirating thrombus fragments into the assembly (10) for removal from the patient's vasculature. The apparatus (10) is able to remove dense thrombus material from within a patient, which cannot be otherwise removed by means of thrombolytic agents.

21 Claims, 3 Drawing Sheets

(56) References Cited

U.S. PATENT DOCUMENTS

| | | | |
|---|---|---|---|
| 6,293,282 B1 * | 9/2001 | Lemelson | A61B 17/32075 128/899 |
| 2003/0083686 A1 * | 5/2003 | Freeman | A61B 5/1411 606/181 |
| 2007/0118165 A1 * | 5/2007 | DeMello et al. | 606/159 |
| 2007/0156164 A1 | 7/2007 | Cole et al. | |
| 2010/0016785 A1 | 1/2010 | Takuma | |
| 2010/0022943 A1 | 1/2010 | Mauch et al. | |
| 2010/0023033 A1 | 1/2010 | Mauch et al. | |
| 2010/0268216 A1 * | 10/2010 | Manwaring et al. | 606/31 |
| 2010/0318117 A1 | 12/2010 | Forsell | |
| 2011/0105947 A1 * | 5/2011 | Fritscher-Ravens | A61B 10/0266 600/567 |

\* cited by examiner

THROMBUS REMOVAL APPARATUS

This application claims the benefit of the filing date of United Kingdom (GB) patent application number 1301428.7, filed Jan. 28, 2013, which is hereby incorporated by reference herein.

TECHNICAL FIELD

The present invention relates to apparatus for removing thrombi from a patient's vasculature.

BACKGROUND ART

There are many systems for treating and removing thrombi from a patient. Traditional methods involve the administration of blood thinning medicaments (thrombolytic agents) which are intended to dissolve thrombus material, which can then be dispersed in the blood stream. Other systems use filters for capturing thrombus material, which can then either be removed along with the filter or dissolved with appropriate medicaments. Yet other systems involve aspiration of thrombus material through a retrieval catheter.

Existing methods are generally successful in removing many types of thrombi but are not normally able to remove thrombi formed of denser material, such as found in older thrombus formations. Such thrombus material does not generally dissolve readily with thrombolytic drugs at physiologically safe concentrations and cannot readily be aspirated into a catheter. Moreover, such thrombi tend to be attached to the vessel wall, with the result that filtration is an ineffective tool for removing them.

A thrombus formation should not be left untreated in the patient given the risks caused by its fragmentation and the fact that the thrombus will generally continue to grow, eventually occluding the vessel in which it is located.

Examples of thrombus capture and removal devices and solenoid operated medical tools can be found in US-2010/0,318,117, US-2010/0,023,033, US-2010/0,022,943, U.S. Pat. No. 5,520,635, WO-02/100,460 and US-2007/0,156,164.

DISCLOSURE OF THE INVENTION

The present invention seeks to provide improved thrombus removal apparatus and a method of removing a thrombus. The preferred embodiments disclosed herein can also provide a thrombus removal device which can be used in cerebral applications.

According to an aspect of the present invention, there is provided thrombus removal apparatus including a catheter having a distal end, a proximal end and an internal lumen; a solenoid coil of conductive material located at or proximate the distal end of the catheter; electrical couplings being connected to the coil; and a piercing element disposed in the internal lumen at the distal end of the catheter; the piercing element being movable in the catheter by application of electrical energy to the solenoid coil.

In an embodiment, the solenoid coil is disposed within a coil section fitted to the distal end of the catheter. The coil section is preferably integral with the catheter, for example by being bonded to the distal end of the catheter or by including one or more of the components forming the catheter. Bonding may be by use of a bonding agent, by laser welding, by friction welding or the like.

In another embodiment, the solenoid coil is formed as a part of the catheter, for instance by being wound around the distal end of an inner layer of the catheter. In this embodiment, there is no distinct coil section. In an example, the solenoid coil may be disposed inside the catheter, for instance within the structure forming the wall of the catheter. In a practical embodiment, the solenoid coil may be sandwiched within inner and outer catheter wall layers.

Preferably, the coil is made from flat strip material. In an embodiment, the coil is wound in helical manner around a substrate forming a layer of the coil section or catheter. The coil may be would in a plurality of layers, in which case the coil may be provided with insulation to prevent electrical shorting between overlapping layers.

In the preferred embodiment, the catheter is an aspiration catheter and the apparatus includes an aspiration unit connectable to the catheter.

The piercing element is advantageously hollow, having a lumen extending therethrough coaxial with the lumen of the catheter. It is preferred that the piercing element includes spaced piercing points. Advantageously, the spaced piercing points are disposed either side of the lumen. There may be a pair of piercing points or more than two, spaced around the lumen.

The piercing element is advantageously formed from a ferromagnetic material or a rare earth metal or a combination of the two. The rare earth element may be neodymium. In some embodiments at least the piercing element is encapsulated in a biocompatible material.

There may be provided a spring to retract the piercing element back into the coil section. In other embodiments this may be achieved by reverse current passed through the coil.

A tether is preferably coupled to the piercing unit, the tether being attached to the catheter or other part of the apparatus, the tether allowing limited movement of the piercing element in the catheter. The tether may be a wire or catheter.

According to another aspect of the present invention, there is provided a method of removing a thrombus from a patient's vasculature, including the steps of:

deploying endoluminally in a patient thrombus removal apparatus including a catheter having a distal end, a proximal end and an internal lumen; a solenoid coil of conductive material located at or proximate the distal end of the catheter; electrical couplings being connected to the coil; and a piercing element disposed in the internal lumen at the distal end of the catheter;

locating the distal end of the catheter and piercing element proximate a thrombus;

activating the solenoid coil by application of electrical energy to the solenoid coil to as to cause the piercing element to strike forwardly into the thrombus, thereby to cause fragmentation of the thrombus.

Advantageously, the method includes the step of applying aspiration to the catheter to aspirate into the catheter thrombus fragments created by the piercing element.

The structure and method disclosed herein provide a device which is able to pierce into a thrombus and cause this to fragment. The piercing element can be made to reciprocate so as to strike the thrombus material repeatedly, thereby contributing to the destruction of the thrombus and its removal. The device can be made very compact and is able to be used in cerebral applications.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the drawings are schematic only and not to scale.

The embodiments of thrombus removal device described herein are in the form of a catheter or sheath (hereinafter referred to generically as a catheter) having a piercing element disposed in the catheter and reciprocally movable within the catheter. The piercing element is moved to extend beyond the distal end of the catheter, so as to strike and cut into a thrombus to cause the latter to fragment. The assembly is able to manufactured with a very small footprint, that is a very small outer diameter, and to be very flexible, enabling the assembly to be used in narrow vessels including cerebral vessels. It will be appreciated the device can also be used for larger vessels and thus manufactured to have a larger diameter.

As will be apparent from the description of the preferred embodiments given below, the apparatus disclosed herein is particularly useful in the removal of established thrombi and other thrombi which are made of particularly dense material, which cannot readily be dissolved by thrombolytic agents or by means of simple aspiration.

Figure 1:
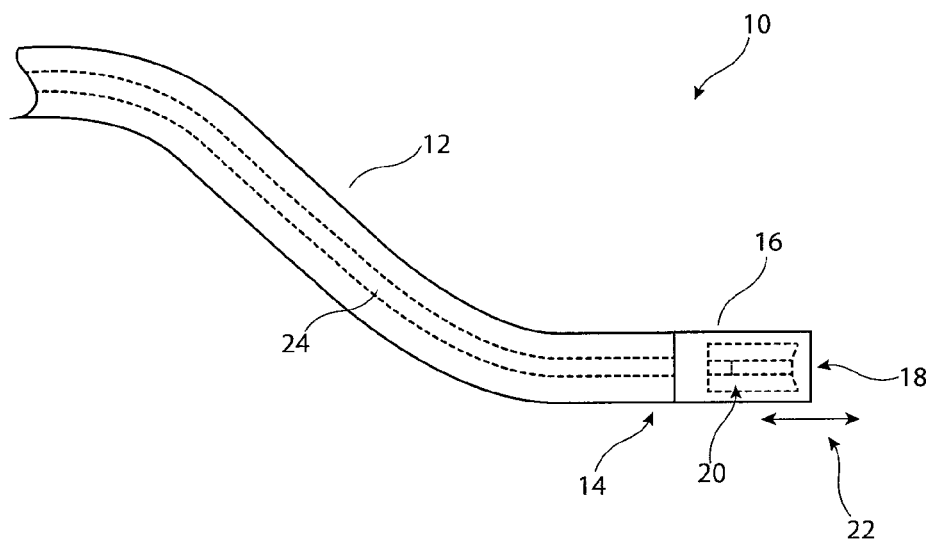
FIG. 1 is a schematic diagram of an embodiment of thrombus removal apparatus.

Referring now to FIG. 1, there is shown the distal end of an embodiment of thrombus removal apparatus 10, which includes a sheath 12 having a proximal end (not visible in FIG. 1) and a distal end 14. At the distal end 14 there is provided a solenoid coil section 16, described in further detail below.

The sheath 12 may be a known sheath or catheter used for introducer assemblies and for this purpose may be a single layer structure or a multi-layer structure including one or more strengthening elements and other components commonly used in the art. The catheter 12, in some embodiments, may incorporate elements of the mechanism, that is the solenoid coil section 16, as described below.

In the embodiment shown in FIG. 1, the solenoid coil section 16 is bonded to the catheter 12 by bonding agent, by laser welding, by friction welding or by any other suitable mechanism.

The solenoid coil section 16 has a generally tubular form with an internal lumen, indicated generally at 18, which aligns with the lumen of the catheter 12. The lumen 18 of the coil section 16 will typically be of round transverse cross-section but this is not necessarily the case as the lumen could have any other transverse cross-section, for instance oval, square, triangular or other polygonal shape. Similarly, the lumen 18 may have an internal diameter the same as the internal diameter of the lumen of the catheter 12, but embodiments may have a different diameter, for instance a larger diameter for reasons described below.

Disposed within the solenoid coil section 16 is a piercing element 20 which is slidably disposed within the coil section 16 and movable in the direction of the arrows 22. Further details of the piercing element 20 are described below.

The piercing element 20 is coupled to a tether 24, which may be a wire or a second catheter.

Figure 2:
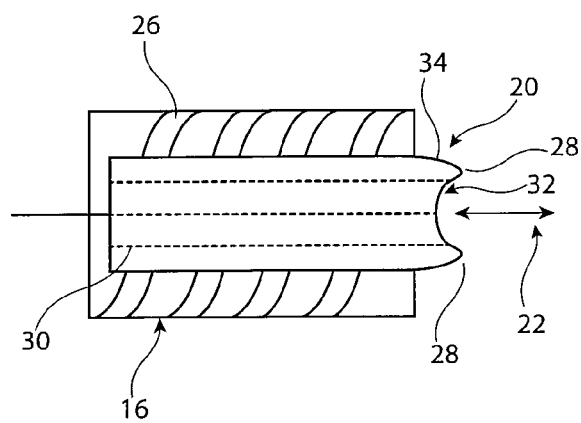
FIG. 2 is an enlarged view in cross-section of a coil section of the catheter of FIG. 1.
Figure 3:
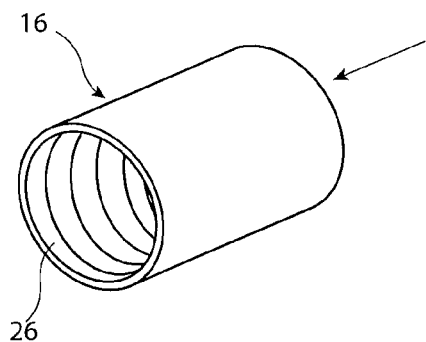
FIG. 3 is an end view of the coil section of FIG. 2.

Referring now to FIGS. 2 and 3, the coil section 16 is preferably made as a three or more component structure, having an inner layer of an electrically insulating material such as a non-conductive polymer, as well as an outer layer typically made of the same material as the inner layer and similarly being non-conductive. Sandwiched between the inner and outer non-conductive layers and in some instances embedded in one of these layers is a solenoid coil 26 which coils in helical manner along the length of the section 16.

The skilled person will appreciate that the solenoid coil 26 will include input and output terminals for connecting an electrical supply to the coil 26. Such terminals will be electrically insulated in a manner which will be readily apparent to the person skilled in the art. In this regard, it is envisaged that there will be disposed on or in the structure of the catheter 12, or of the tether 24, electrical conductors for the supply and return paths of electrical current to the coil 26. Such conductors could, for example, be disposed within the structure of the multi-layer catheter 12 or on the internal surface of the catheter 12 and spaced from one another or insulated so as not to short electrically. In the case of the tether 24, this could comprise electrical conductors to the coil 26 and in other embodiments the electrical conductors could be provided on the outside of, on the inside of or encapsulated within the wall of a catheter tether 24. The coil 26 may be a single layer but is preferably provided in multiple layers, in which case the coil will be provided with insulation to prevent electrical shorting of the overlapping or adjacent turns of the coil.

The coil 26 is preferably made in the form of a flat strip of material, although in other embodiments could be a wire of round cross-section. Use of a flat strip enables the production a thin-walled coil section 16, useful in minimising the overall outer diameter of the apparatus 10. A flat strip can provide a greater cross-sectional area of conductor compared to a round wire of similar thickness. In the preferred embodiment, the coil 26 has a width of less than 1.0 mm and a thickness of less than, and preferably substantially less than, 1.0 mm. These dimensions would be suitable for a solenoid coil section 16 having a length of up to or less than 5 mm. However, in some embodiments, the coil section can be substantially shorter, for example being 1 or 2 mm in length, in which case the coil 26 could be made of strip material of substantially less width than 1 mm. It is preferred, in this regard, that the coil 26 has at least 4 or 5 turns or more within the length of the solenoid coil section 16.

The coil section 16 is preferably substantially rigid, such that the lumen 18 within the coil section 16 is stable in terms of its longitudinal shape and its diameter when in situ in a patient. A stable section 16 also ensures stability of the coil 26 and of the electromagnetic field generated by the coil during operation of the apparatus 10, although this is not considered an essential advantage.

FIG. 2 shows the piercing element or plunger 20 in better detail. The piercing element 20 is preferably of generally tubular form with an outer shape which conforms to the inner wall of the coil section 16, so as to be a close fit within the coil section 16 and yet able to reciprocate backwards and forwards in the direction of arrows 22 with little or no friction. Thus, the piercing element 20 will typically have a round cylindrical form, although may be oval, square, triangular or other shape consistent with the internal shape of the section 16.

It is preferred that the piercing element 20 has a length which is no more than the length of the coil section 16, such that the piercing element 20 is able to reside fully within the assembly 10 and most preferably within the coil section 16. It is not excluded, however, that the piercing element 20 may extend partially within the catheter 12 and in some instances may also extend beyond the distal end of the coil section 16, in a manner similar to that shown in FIG. 2. However, this latter configuration is not preferred as it would leave the piercing jaws or blades 28 of the piercing element (described in further detail below) exposed, whereas they are preferably fully housed in the section 16 until their use.

In the preferred embodiments, the piercing element 20 includes an internal lumen 30 extending for the entirety of its length. In the case where the tether 24 is a secondary catheter, this will be aligned with the lumen 30 of the piercing element 20 so as to provide a continuous lumen from the distal end of the piercing element 20 all the way to the proximal end of the assembly 10, the latter remaining outside the patient during the medical procedure, as explained below.

The piercing element 20 includes, in this embodiment, first and second blades or jaws 28 which are disposed either side of the lumen 30 and thus at opposite sides of the piercing element 20.

The blades 28 may be in the form of circumferentially rounded cutting elements or elements of narrow width, with sharp distal ends. The purpose of the blades 28 is to dig into thrombus material so as to cause this to fragment. In the example shown, the blades 28 are formed by removal of parts of the wall of the piercing element 20 by cutting sides recesses 32 in the distal end of the piercing element to leave the longitudinally extending blades 28. The blades 28 have sharp apices produced by bevelling the sides 34 of the wall on the element 20.

In this example, piercing element 20 includes two blades 28, although in other embodiments there may be a different number of blades. There may, for example, be provided four blades circumferentially spaced around the distal end of the piercing element 20, as there may be three or more than four. Similarly, a single blade 28 may be provided in some embodiments.

The piercing element 20 is made of a ferromagnetic or paramagnetic material, such as iron or an iron alloy, but more preferably a rare earth metal such as neodymium. The piercing element 20 may be sealed by a coating of biocompatible material on all of its exposed surfaces, although where it is coated this is preferably by total encapsulation of the element 20. A coating of this nature enables the use of otherwise non-biocompatible materials in the manufacture of the piercing element 20. It is to be understood that the piercing element 20 could be made of a combination of electromagnetic materials or of one or more electromagnetic materials with other materials.

Figure 4:
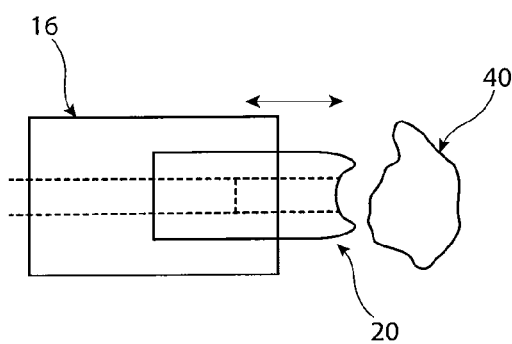
FIG. 4 is a schematic view of the distal end of the assembly of FIG. 1 showing the piercing element in an extended piercing position.

Referring now to FIG. 4, there is shown in schematic form a view of the solenoid coil section 16 in operation. Of course, the catheter 12 and other elements of the assembly 10 would be disposed proximally of the coil section 16, as shown in FIG. 1.

The apparatus 10 is disposed within the vasculature of a patient adjacent a thrombus formation 40, which would typically be attached to the vessel wall. In this regard, the assembly 10 can be deployed endoluminally through the patient in a manner conventional in the art. Once located adjacent the thrombus 40, preferably in abutment against it, an electric current is fed into the coil 26 of the apparatus 10, which generates an electromagnetic field causing the piercing element 20 to strike forwardly and into the thrombus 40. It will be appreciated that the tether 24 will maintain hold of the piercing element 20 and is of a design and dimension to ensure that the piercing element 20 cannot be driven electromagnetically completely out of the coil section 16. In some embodiments, the piercing element 20 may include a flange or stop shoulder which co-operates with a corresponding flange or shoulder on the inside surface of the coil section 16 to limit the amount by which the piercing element 20 can extend out of the coil section 16.

When the piercing element 20 is driven into the thrombus 40, the blades 28 will cut away at the thrombus material 40, causing this to fragment. The direction of current feed into the coil 26 can be changed in alternating current manner, thereby to switch the electromagnetic field repeatedly and cause the piercing element 20 to reciprocate backwards and forwards within the coil section 16. This will cause the piercing element 20 to strike into the thrombus 40 repeatedly, so as to break up the thrombus 40 gradually, until it has been entirely or substantially entirely removed.

In another, and preferred, embodiment there is provided a spring coupled to the piecing element 20 and to a part of the coil section or catheter, which is put under tension when the piercing element is made to extend out of the coil section 16, thereby to bias the piecing element 20 back into the section 16. With such an arrangement, removal of any electromagnetic field produced by the coil 26 will result in the piercing element 20 being retracted into the coil section 16.

The thrombus fragments may in some instances be permitted to disperse within the patient's blood stream, to be broken down by natural body mechanisms. In some embodiments a suitable filter assembly may be disposed within the patient's vasculature downstream of the apparatus 10 and in particular of the cutting section 16, 20 to catch the thrombus fragments. Preferably, however, the apparatus 10 is provided with an aspiration facility, as shown in schematic form in of FIG. 5. In this Figure, the assembly 10 includes the components described above.

At the proximal end 50 of the catheter 12 there is provided an external manipulation unit 52 which includes elements conventional in the art, such as haemostatic valves, flushing ports and so on, as well as a solenoid control system 52. The control system 52 supplies current to the coil 26 under the control of suitable switches or other control elements, the nature of which will be immediately apparent to a person skilled in the art.

Figure 5:
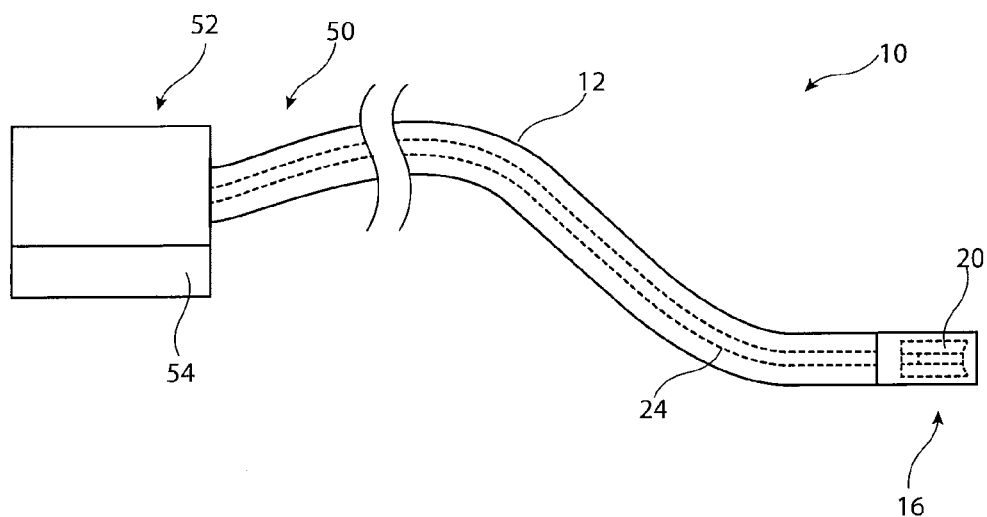
FIG. 5 is a schematic diagram of another embodiment of thrombus removal assembly incorporating an aspiration device.

The embodiment of FIG. 5 also includes a pump 54 coupled to the catheter 12 and/or to the secondary catheter 24 when provided. Pump 54 is actuated preferably during the process of operation of the piercing element 20, so as to create suction at the distal end of the apparatus 10 for extracting thrombus fragments by aspiration through the catheter 24 and/or the catheter 12. Thus, the thrombus 40 can be removed from the patient by means of the apparatus 10 and without needing any additional components, although a filter or the like may still be provided.

The system 10 is thus able to remove a thrombus 40 from within a patient's vessel even when the latter is constituted by dense thrombus material not able to be dissolved by traditional thrombolytic agents at safe concentration levels.

In the embodiments described above, the coil section 16 is a distinct component from the catheter 12. Other embodiments, on the other hand, incorporate the solenoid coil 26 within the structure of the catheter 12 itself. More specifically, the catheter 12 may typically be formed as a multi-layer component including an inner polymeric layer, and intermediate layer which would include the coil 26 and an outer polymeric layer encapsulating the intermediate layer. In this example, the coil 26 would be sandwiched between the inner and outer layers of the catheter and an integral part of the structure. The catheter may still include strengthening elements along the majority of its length, such as a strengthening coil or braiding and in this regard it is envisaged that the strengthening elements may also provide the electrical conductors for feeding electrical current into the coil 26.

A catheter of this nature could be manufactured on a mandrel, in which the first layer disposed on the mandrel will be the inner catheter layer, whereupon any strengthening elements and the coil 26 are disposed over the inner layer, for example by winding; and then an outer polymeric layer applied over the assembly. Application may be by any of the known methods.

When the coil section 16 is a part of the catheter 12, there may be provided additional strengthening at the section 16 to cause this to be substantially rigid.

In all of the above-described embodiments, the lumen of the coil section 16 may be slightly larger than the lumen of the catheter 12, and/or of a different shape, to create an internal shoulder between the coil section 16 and the catheter 12 for use as a stop to movement of the piercing element 20 into the assembly 10, particularly upon application of a "reverse" electromagnetic field to the coil 16.

The skilled person will appreciate that above are described only some embodiments of the present invention and that modifications or additions will be readily apparent to the skilled person having regard to the teachings herein and the scope of the claims.

The invention claimed is:

1. Thrombus removal apparatus including a catheter having a distal end, a proximal end and an internal lumen; a solenoid coil of conductive material adapted to be positioned within an endoluminal passage and located at or proximate the distal end of the catheter; electrical couplings being connected to the coil; and a piercing element disposed in the internal lumen residing at least partially within the solenoid coil at the distal end of the catheter; a distal portion of the piercing element being movable in the catheter by interaction of a proximal portion of the piercing element with an electromagnetic field induced by application of electrical energy to the solenoid coil; and including a restriction device coupled to the piercing element and extending proximally from a proximal end of the piercing element to be coupled to the catheter or other part of the apparatus, the restriction device allowing limited distal movement of the piercing element in the catheter and being configured to retain at least a portion of the piercing element within the solenoid coil.

2. Thrombus removal apparatus according to claim 1, wherein the piercing element is hollow.

3. Thrombus removal apparatus according to claim 2, wherein the piercing element includes a lumen extending therethrough coaxial with a lumen of the catheter.

4. Thrombus removal apparatus according to claim 1, wherein the piercing element includes spaced piercing points.

5. Thrombus removal apparatus according to claim 1, wherein the piercing element is formed from a ferromagnetic or paramagnetic material.

6. Thrombus removal apparatus according to claim 1, wherein the piercing element is formed from iron, an iron alloy or a rare earth metal or alloy.

7. Thrombus removal apparatus according to claim 1, wherein the piercing element is encapsulated in a biocompatible material.

8. Thrombus removal apparatus according to claim 1, wherein the catheter is an aspiration catheter and the apparatus includes an aspiration unit connectable to the catheter.

9. Thrombus removal apparatus according to claim 1, wherein the solenoid coil is disposed within a coil section fitted to or disposed at the distal end of the catheter.

10. Thrombus removal apparatus according to claim 9, wherein the coil section is integral with the catheter.

11. Thrombus removal apparatus according to claim 9, wherein the coil section is bonded to the distal end of the catheter.

12. Thrombus removal apparatus according to claim 11, wherein the coil section is bonded by one of: a bonding agent, laser welding or friction welding.

13. Thrombus removal apparatus according to claim 1, wherein the coil section includes one or more of the components forming the catheter.

14. Thrombus removal apparatus according to claim 13, wherein the coil is wound around a part of the distal end of the catheter.

15. Thrombus removal apparatus according to claim 14, wherein the solenoid coil is disposed within a wall of the catheter.

16. Thrombus removal apparatus according to claim 15, wherein the catheter is provided with inner and outer catheter layers and the solenoid coil is sandwiched within the inner and outer catheter layers.

17. Thrombus removal apparatus according to claim 1, wherein the solenoid coil is formed as a plurality of layers of coil.

18. Thrombus removal apparatus according to claim 1, wherein the solenoid coil is provided with electrical insulation.

19. Thrombus removal apparatus according to claim 1, wherein the proximal portion of the piercing element is fixedly connected to the distal portion of the piercing element; and wherein the piercing element comprises a circumferential blade extending longitudinally from the distal end of the piercing element.

20. Thrombus removal apparatus including a catheter having a distal end, a proximal end and an internal lumen; a solenoid coil of conductive material adapted to be positioned within an endoluminal passage and located at or proximate the distal end of the catheter; electrical couplings being connected to the coil; and a piercing element disposed in the internal lumen residing at least partially within the solenoid coil at the distal end of the catheter; a distal portion of the piercing element being movable in the catheter by interaction of a proximal portion of the piercing element with an electromagnetic field induced by application of electrical energy to the solenoid coil; wherein the proximal portion of the piercing element is fixedly connected to the distal portion of the piercing element; and including a tether coupled to the piercing element, the tether being attached to the catheter or other part of the apparatus, the tether allowing limited distal movement of the piercing element in the catheter and being configured to retain at least a portion of the piercing element within the solenoid coil.

21. Thrombus removal apparatus according to claim 20, wherein the tether is a wire or catheter.

* * * * *